(12) United States Patent
Cancio (10) Patent No.: US 7,163,505 B1
(45) Date of Patent: *Jan. 16, 2007

(54) THERAPEUTICALLY BENEFICIAL MOVABLE MAGNETIC FIELDS

(76) Inventor: Humberto Cancio, 7731 SW. 32 St., Miami, FL (US) 33155

( * ) Notice: Subject to any disclaimer, the term of this patent is extended or adjusted under 35 U.S.C. 154(b) by 0 days.

This patent is subject to a terminal disclaimer.

(21) Appl. No.: 11/295,377

(22) Filed: Dec. 6, 2005

Related U.S. Application Data (63) Continuation-in-part of application No. 10/885,158, filed on Jul. 6, 2004, now Pat. No. 6,971,983.

(51) Int. Cl.
*A61N 2/00* (2006.01)

(52) U.S. Cl. .......................................... 600/9
(58) Field of Classification Search ................ 600/9–15
See application file for complete search history.

(56) References Cited

U.S. PATENT DOCUMENTS

| | | | | |
|---|---|---|---|---|
| 4,537,181 A | * | 8/1985 | Shalhoob et al. | ............... 600/9 |
| 4,727,857 A | * | 3/1988 | Horl | ............................. 600/15 |
| 4,744,350 A | | 5/1988 | Sato | |
| 5,084,003 A | | 1/1992 | Susic | |
| 5,453,073 A | * | 9/1995 | Markoll | ........................ 600/14 |
| 5,632,720 A | | 5/1997 | Kleitz | |
| 5,667,469 A | * | 9/1997 | Zhang et al. | .................. 600/9 |
| 5,788,624 A | | 8/1998 | Lu et al. | |
| 5,817,000 A | | 10/1998 | Souder | |
| 6,001,055 A | | 12/1999 | Souder | |
| 6,231,497 B1 | | 5/2001 | Souder | |
| 6,663,557 B1 | * | 12/2003 | Werny | ......................... 600/15 |
| 6,971,983 B1 | | 12/2005 | Cancio | |
| 2004/0097781 A1 | * | 5/2004 | Ichikawa et al. | .............. 600/9 |

* cited by examiner

*Primary Examiner*—John P. Lacyk
(74) *Attorney, Agent, or Firm*—Malloy & Malloy, P.A.

(57) ABSTRACT

The present invention relates to a therapeutically beneficial assembly utilizing one or more moveable magnetic fields passing through a treatment area, which is dimensioned and configured to accommodate a user in a standing, walking and/or running orientation therein. A generating assembly comprises at least one but preferably at least two magnetic arrays each mounted in moveable relation to the treatment area and comprising a MOVABLE base having a plurality of magnets connected thereto and moveable therewith. The magnetic arrays are disposed an structured to generate different magnetic fields moveable through said treatment area in a common direction such that the user therein is disposed for maximum or predetermined exposure to the moveable magnetic fields.

27 Claims, 6 Drawing Sheets

THERAPEUTICALLY BENEFICIAL MOVABLE MAGNETIC FIELDS

CLAIM OF PRIORITY

The present application is a Continuation-In-Part application of United States patent application having Ser. No. 10/885,158 filed Jul. 6, 2004, incorporated herein in its entirety by reference, which is set to mature into U.S. Pat. No. 6,971,983 on Dec. 6, 2005.

BACKGROUND OF THE INVENTION

1. Field of the Invention

This invention relates to an assembly for generating one or more movable magnetic fields which communicate with a treatment area and a user therein. The treatment area, as defined in at least some of the preferred embodiments of the assembly is disposed, dimensioned and configured to allow the user to assume an upright, standing, walking or running orientation and receive therapeutic benefit by being exposed to the magnetic fields continuously passing through the treatment area in a common direction.

2. Description of the Related Art

It has long been recognized and generally well-settled that exposing the body of both humans and animals to a magnetic field offers some therapeutic benefits. Clearly, it has been established that the bodies of animals, including humans, are capable of conducting electricity. As such, a variety of healthcare treatments, methods and devices incorporating the use of magnetic fields have been devised and tested. In years past for example, it was even believed that the health of sailors who traveled across the seas in wooden ships was improved, due at least in part, to exposure to the earth's magnetic field, especially when ships traveled in either an easterly or westerly direction.

Known, modern day applications of magnetism and/or the generation of magnetic fields includes devices which allow a magnetic flux to penetrate into the body typically at predetermined localized areas. More specifically, magnetic devices and structures intended for therapeutic use include watches, rings, bracelets, vests, belts, shoes and a variety of other articles. In addition, furniture and body support devices such as cushions, mattresses, beds, etc. have also been utilized in combination with magnets. Common to most, if not all, of the above-noted category of magnetic devices is the incorporation of one or more magnets located in a position or orientation which facilitates the exposure of a specific body portion of an individual to a substantially stationary magnetic field.

Assuming that magnetic treatment of the type set forth above does have therapeutic value and benefits, there are continuing questions relating to the significance of such therapeutic benefits, especially when only a localized area or body portion is being exposed to a magnetic field or magnetic flux. It has further been suggested that devices worn on the body of individuals may, in fact, result in certain harmful effects such as swollen or irritated joint areas such as the wrist, finger joints, etc.

Perhaps even more questionable, is the use of magnetically treated products which are intended to be orally consumed, such as magnetized drinking water. It is suggested that the practice of consistently drinking water that has been magnetized may have some effect in the prevention and treatment of certain ailments. It is believed that the therapeutic benefits associated therewith are limited due to the rapid passage or circulation of the water through the body. As a practical matter, the effect of magnetizing drinking water after a certain period of time is significantly lessened.

In order to overcome many, if not all, of the disadvantages and problems associated with both localized magnetic devices and consumable magnetized products, it is suggested by the inventor hereof that exposing animals, including humans, to a continuously moving magnetic field, may provide a longer lasting and overall greater therapeutic benefit to those individuals who are exposed, even if for relatively brief time periods. Further, if any such system or assembly were developed that incorporates the use of one or more moving magnetic fields, it would be preferable if it were applied and/or structured such that a user or individual being treated is in an upright position, and ideally, if while so oriented the treated individual may even exercise, i.e., be involved in a prescribed or selective movement such as walking, running, jogging, etc. In this manner, any disadvantages associated with magnetic devices intended to treat localized areas such as bracelets, rings, shoes, etc. would be overcome through the application of one or more magnetic fields which preferably pass through a treatment area in which the treated individual is walking, jogging or at least oriented in an upright position. Further, if any such system or assembly were developed that incorporates the use of one or more moving magnetic fields, it would be preferable if it also offers an ability to adjust the physical and operative characteristics of the generated magnetic fields to allow increased areas of the torso, legs, arms, etc. to be exposed during the continuous and/or other predetermined movement of the generated magnetic fields as they pass through the treatment area. In addition, if any such improved assembly were developed, it would also preferably be structured to expose a user to one or more therapeutically beneficial magnetic fields structured to have sufficient versatility in the application thereof to enable its use by individuals of all ages and sizes.

SUMMARY OF THE INVENTION

The present invention is directed to an assembly structured to generate one or more movable magnetic fields and expose a user thereto, while the user is within an at least partially defined treatment area. Further, the various preferred embodiments of the assembly of the present invention comprises a generating assembly structured to generate the one or more magnetic fields, such that the magnetic fields move through the treatment area and expose the user therein to the therapeutic benefits created thereby. Accordingly, the assembly of the present invention is intended to overcome many if not all of the disadvantages and problems associated with the conventional devices or assemblies which attempt to localize a magnetic field relative to a certain portion of an individual's body.

In contrast, the magnetic fields produced by the generating assembly of the various preferred embodiments of the present invention are maintained, while in use, in substantially continuous motion. Further the generated magnetic fields pass through the treatment area in a predetermined manner such as, but not limited to, movement of the magnetic fields in a common direction and along a substantially linear path of travel. Accordingly, substantially the entire torso and/or other portions of a user's body are exposed to the moving magnetic fields in a manner intended to maximize the therapeutic benefits to the user.

More specifically, the assembly of the present invention, and at least some of the preferred embodiments thereof, comprise a frame disposed adjacent to and at least partially defining the treatment area. The frame and accordingly the treatment area is dimensioned, configured and otherwise structured to facilitate the user assuming at least an upright orientation. While the user is so disposed, the one or more generated magnetic fields move through the treatment area and relative to the user, in a substantially common and linear direction, depending on the particular one or more embodiments of the present invention being used. Accordingly, major and/or predetermined portions of the user's body are exposed to the magnetic fields.

Also, one or more preferred embodiments of the present invention incorporate the use of a support platform disposed within the treatment area in supporting relation to the user. The support platform may be structured to facilitate movement of the user, at least to the extent of the user assuming a walking or running orientation as desired. By way of example only, the moveable support platform may comprise a treadmill assembly. Therefore, practical application of the present invention may include concurrent movement of the user within the treatment area while being exposed to the one or more movable magnetic fields. In yet another preferred embodiment of the present invention, the aforementioned moving orientation of the user, while in the treatment area, may be accomplished by providing the frame with a moveable support assembly. As such, the moveable support assembly is structured to allow movement of the frame and accordingly the treatment area over a supporting surface. The force required to move the frame and treatment area may be supplied by the user walking or running along the supporting surface while pushing or otherwise propelling the frame. This latter described preferred embodiment would eliminate the need of a movable support platform, such as a treadmill assembly, as described above.

The generating assembly comprises at least one but preferably a plurality of at least two magnetic arrays movably mounted adjacent the treatment area and in communication therewith. In a most preferred embodiment, each of the magnetic arrays is movably connected to or otherwise disposed and structured with the frame in predetermined relation to one another and to the treatment area. When so disposed, the respective magnetic fields generated by the magnetic arrays will be directed towards the interior of the treatment area and the user disposed therein. Each of the magnetic arrays comprises a plurality of magnets disposed in predetermined relation to one another and collectively mounted on a moveable base.

While the plurality of magnets as well as the base of each magnet array may assume a variety of different structural and operative configurations, one preferred embodiment includes the base of each of the magnetic arrays being in the form of a continuously configured conveyor structure movable along a continuous, closed path of travel. When activated, the base of each magnetic array is maintained in continuous motion such that the plurality of magnets associated therewith move and generate a magnetic field. As set forth above, the generated magnet fields pass through the treatment area so as to expose major and/or predetermined portions of a user's body thereto.

Also, in order to accomplish the desired therapeutic benefit, one or more of the preferred embodiments of the present invention comprise two magnetic arrays disposed on opposite sides of the treatment area and the user disposed therein. Also, when the magnetic arrays include the base comprising a continuously movably conveyor-type structure, as set forth above, they are preferably disposed and structured to rotate or move in opposite directions. Therefore, the user who is located substantially between both of the concurrently moving magnetic arrays is concurrently exposed to the magnetic flux generated by each of the magnetic arrays. As a result a user within the treatment area is exposed to at least two continuously moving magnetic fields passing in a common direction through the treatment area and on opposite sides of the user.

In preferred embodiments of the present invention that include a plurality of magnetic arrays, optimal conditions for accomplishing the maximum therapeutic value of the generated magnetic fields may involve the synchronized movement of the magnetic arrays as well as the cooperative orientation of the plurality of magnets on each of the movable bases. As set forth above, the plurality of magnets associated with each of the magnetic arrays may vary in structure, size, configuration and operation. Accordingly, each of the plurality of magnets may be permanent magnets, wherein the respective poles thereof are cooperatively positioned relative to the remaining plurality of magnets associated with the same magnetic array. Predetermined and/or selective positioning of the plurality of magnets and the base associated therewith serve to produce a magnetic field of predetermined size, configuration, orientation and disposition. Also, a selective or predetermined variation of the generated magnetic fields may be created in order to add significant versatility in exposing the user to the continuously moving magnetic fields, while in a preferred or prescribed orientation in the aforementioned treatment area.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As shown in the accompanying drawings, the present invention is directed to an assembly generally indicated as 10 structured to expose a user, generally indicated as 12, to one or more moving magnetic fields for the purpose of gaining the therapeutic benefits and/or potentially curative properties thereof. With primary reference to FIG. 1, one preferred embodiment of the assembly of the present invention includes a frame generally indicated as 14. The frame 14 is dimensioned, configured and has an overall structure to at least partially define a treatment area generally indicated as 16. The treatment area 16 is dimensioned and configured to allow the user 12 to assume an upright or other orientation. As will be explained hereinafter, with reference to additional preferred embodiments, the frame and treatment area are further structured to allow the user 12 to assume a walking, jogging, or running orientation concurrently to being exposed to the one or more moving magnetic fields.

Figure 1:
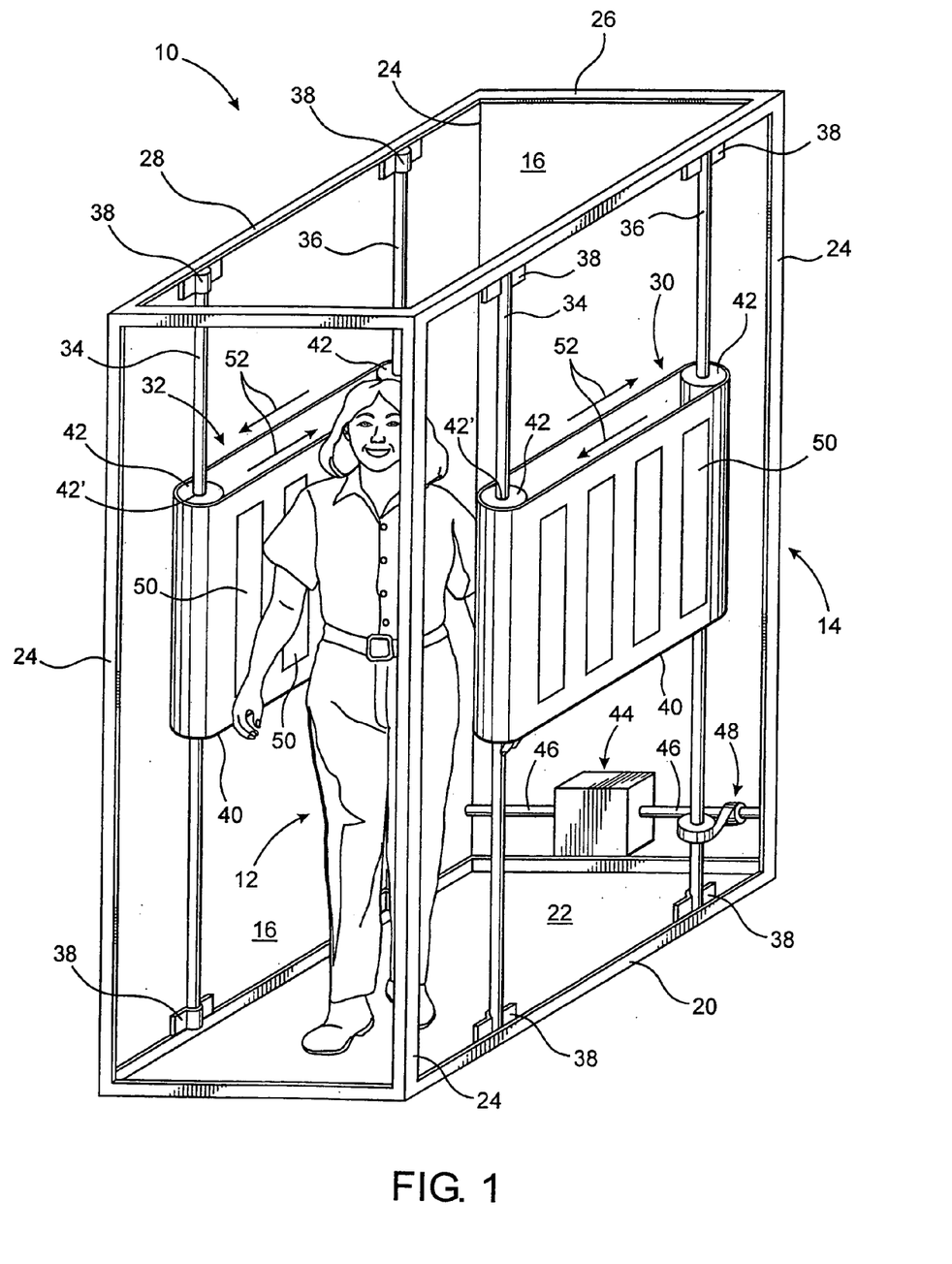
FIG. 1 is a perspective view of the assembly of the present invention structured to include a plurality of generating assemblies each of which are structured to generate separate but cooperative magnetic fields to which a user is exposed while in a treatment area.

It is emphasized that the frame 14 may assume a plurality of different structures, dimensions and configurations, any of which are capable of at least partially defining the treatment area 16 which enables the user 12 to assume the aforementioned upright stationary or moving orientation. Accordingly, by way of example, the preferred embodiment of the frame 14 as represented in FIG. 1 includes a bottom section 20 disposed in somewhat surrounding relation to a support platform 22. The support platform 22 may be defined by the floor or ground surface on which the frame 14 is disposed, in which case the bottom frame portion 20 is open. Alternatively, the support surface 22 may comprise a separate flooring or platform structure connected to or otherwise associated with the frame 14.

In addition, the frame 14 preferably includes a plurality of vertically or otherwise oriented upright stanchions 24 connected to the bottom frame portion 20 and extending upwardly therefrom. An upper frame portion 26 may be disposed and configured to define the periphery of an upper opening 28 communicating directly with the interior of the frame 14 and/or the treatment area 16. Another structural modification of the frame 14 may be the enclosure of the opening 28 by means of one or more covering panels. Similarly the various side portions of the frame 14 disposed between the upright stanchions 24 are preferably open but may be at least partially enclosed by one or more panels or panel segments. When fully or at least partially enclosed, the enclosing panels or panel segments may be formed from transparent, translucent or opaque materials. The openly configured frame 14 of course provides the advantage of having a free circulation of ambient air passing through the treatment area 16 as well as facilitating visual access to and by the user 12 during a treatment procedure.

The aforementioned one or more moving magnetic fields are established by a generating assembly comprising at least one magnetic array generally indicated as 30 and more practically a plurality of at least two magnetic arrays such as 30 and 32. In the preferred embodiment of FIG. 1, each of the magnetic arrays 30 and 32 are located adjacent the treatment area 16 so as to provide correspondingly generated magnetic fields which communicate directly with the interior of the treatment area 16 and the user 12 therein. Also, each of the magnetic arrays 30 and 32 may be connected to the frame 14 or be otherwise mounted immediately adjacent thereto and preferably on opposite sides of the treatment area 16 as demonstrated. When connected directly to the frame 14, each magnetic array 30 and 32 may include spaced apart support rods 34 and 36 attached to the frame 14 by journal or bearing assemblies 38 located at opposite ends of the support rods 34 and 36. The journal or bearing assemblies 38 serve to fixedly or rotationally connect the respective support rods 34 and 36 to the lower frame portion 20 and the upper frame portion 26.

In addition to the above, each of the magnetic arrays 30 and 32 include a base 40 preferably, but not necessarily, in the form of a conveyor structure having a closed or continuous configuration. Each of the bases is interconnected to and between the support rods 34 and 36 by rollers or equivalent structures as at 42. Moreover, each base 40 is interconnected by appropriate linkage to a drive assembly, generally indicated as 44. The drive assembly 44 may be in the form of an electrically or otherwise powered drive motor having one or more power take-off shafts 46 interconnected by appropriate linkage 48 to at least one of the support rods, as at 36. Activation of the drive assembly 44 causes a driving rotation of both of the power take-off shafts 46 and concurrent rotation of at least one of the support rods 36 by means of the interconnecting linkage 48. As one example of the structure and function of the embodiment of FIG. 1, a corresponding one of the rollers 42 may be fixedly connected to and rotate with the support shaft 36, wherein the opposite roller 42 may be interconnected to the support rod 34 by means of a bearing assembly 42'. Therefore continuous operation of the drive motor/drive assembly 44 will cause a continuous rotation of each of the support rods 36 and corresponding rollers 42. Concurrently the support rods 34 will remain fixed while the rollers 42 associated therewith will be allowed to rotate, because of their attachment to the support rods 34 by bearing structures 42'. A continuous rotation of conveyor-like bases 40 will result in the production of continuously moving magnetic fields as will be explained in greater detail hereinafter.

Figure 3:
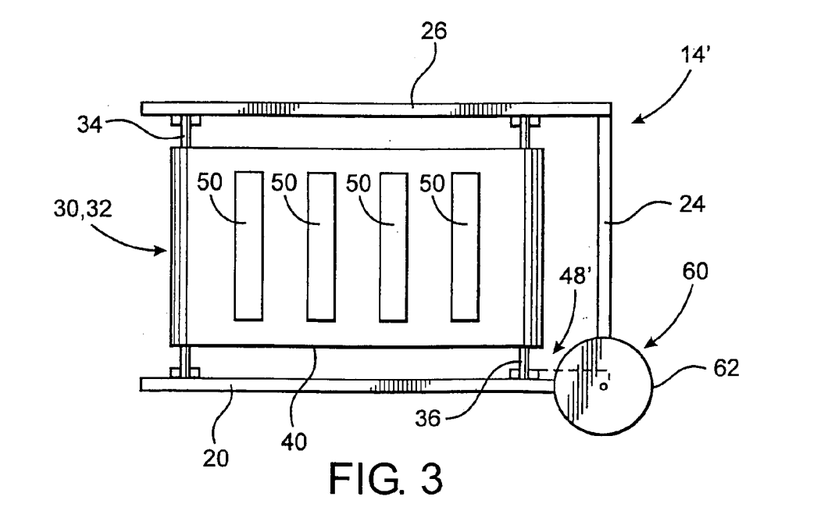
FIG. 3 is a side view in partial cutaway including at least one generating assembly similar to that represented in the embodiment of FIG. 1 but clearly adaptable to the embodiment of FIG. 2.

As clearly represented in FIGS. 1 and 3 each of the magnetic arrays 30 and 32 include a plurality of magnets 50 mounted on the exterior face of and moveable with corresponding ones of the bases 40. When the drive assembly 44 is activated, the bases 40 rotate, preferably in predetermined opposite directions, as indicated schematically by the directional arrows 52. The plurality of magnets 50 may comprise permanent magnets disposed in spaced relation to one another along the length of the outer face of the base 40 and are preferably sufficient in number to cover substantially the entire length of the outer face or at least a predetermined majority of the length thereof. The plurality of magnets 50 may differ in number, size, configuration, etc. to accomplish the primary purpose of generating a magnetic field. As should be apparent the cooperative disposition of each of the plurality of magnets 50 associated with the different magnetic arrays 30 and 32 are such that the different magnetic fields pass substantially transversely through the treatment area 16, while exposing user 12 thereto.

While the plurality of magnets 50 are initially described as being permanent magnets, it is intended that the spirit and scope of the present invention also include the plurality of magnets 50 being defined by electromagnets. When so structured, the various poles and the resulting magnetic flux generated by each of the electromagnets 50 may be varied by regulating current flow thereto. Regardless of the structuring of the plurality of magnets 50 being either permanent or electromagnets, the intensity of the generated magnetic flux must be sufficient to expose the user 12, when located within the treatment area 16, to the continuously moving magnetic fields generated by each of the magnetic arrays 30 and 32.

Accordingly, the disposition of the plurality of magnets 50, the movement of the individual bases 40 and the resulting magnetic fields generated thereby may be synchronized. As indicated, such synchronization may be accomplished by current flow regulation to the plurality of magnets 50, when such are electromagnets. Also, the operation of the drive assembly 44, the location and structure of the power take-off shafts 46 and the location and operation of the interconnecting linkage 48 may also serve to accomplish a predetermined synchronization of the moving magnetic fields. While not specifically shown in FIG. 1, an appropriate interconnecting linkage 48 also serves to drivingly interconnect a corresponding one of the power take-off shafts 46 with the support rod 36 associated with the magnetic array 32.

Figure 2:
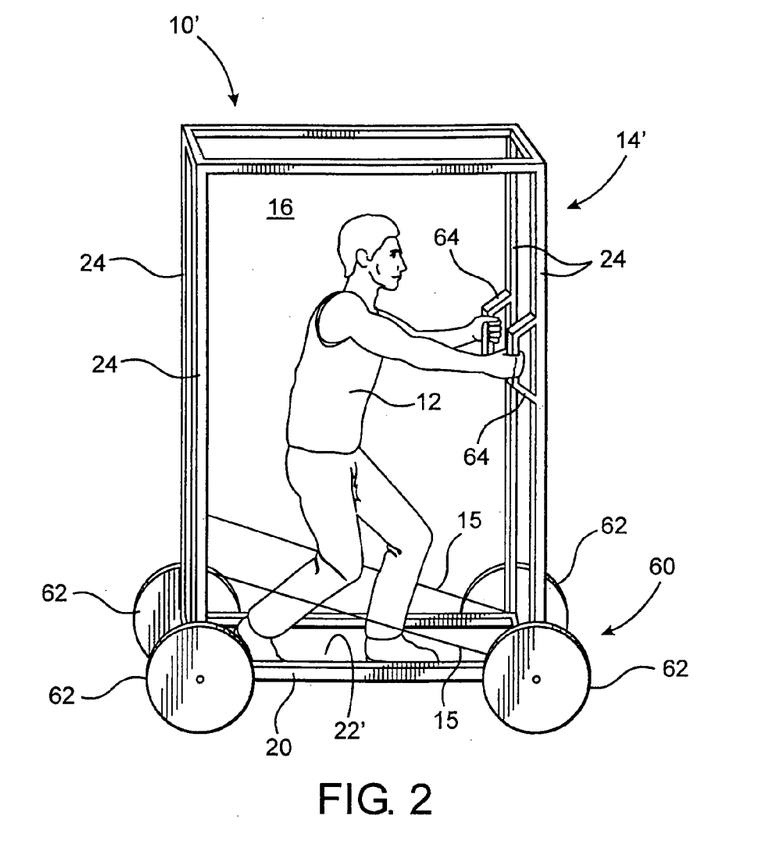
FIG. 2 is a perspective view of yet another preferred embodiment of the assembly of the present invention.

Yet another preferred embodiment of the present invention is represented in FIGS. 2 and 3. Moreover, a frame 14' at least partially establishes or defines the boundaries of the treatment area 16 so as to allow the user 12 to maintain the preferred upright position. The structural and functional features of the frame 14' are such as to facilitate the user assuming a walking, jogging and/or running orientation, while in the upright position as demonstrated. More specifically, the frame 14' includes a movable support assembly generally indicated as 60, including a plurality of wheels, rollers, or other appropriate movable support structure 62 connected to the lower portion 20 of the frame 14'. As such, the frame 14' is mobile and is powered by the walking, jogging, running, etc. motion of the user 12, while exerting a pushing or other appropriate force on the frame 14'. Gripping handles or other appropriate structures 64 are provided for this purpose. Concurrently to exerting the propelling force on the frame 14', the user 12 moves across the support surface 22' on which the frame 14 and the movable support assembly 60 are positioned. Therefore, the lower portion 20 of the support frame 14 is open to allow the feet of the user 12 to engage the supporting surface 22', which may be flooring, ground surface, etc. Additional cross braces 15 may be added to the frame 14' for purposes of maintaining a sufficient structural integrity of the frame 14', which may be required due to the forced movement thereof as the user 12 across the support surface 22'.

While not specifically represented in FIG. 2, frame 14' includes at least one but preferably a plurality of two magnetic arrays 30 and 32 located on opposite sides of the frame 14' similar to that demonstrated in the preferred embodiment of FIG. 1. As with each of the magnetic displays 30 and 32 of the embodiment of FIG. 1, the same or appropriately equivalent magnetic arrays 30 and 32 are demonstrated in FIG. 3 and include a movable base 40 and a plurality of magnets 50 as previously discussed. However, one distinguishing feature of the embodiment of FIGS. 2 and 3 is the forced, driving rotation of each of the plurality of magnetic arrays 30 and 32 by the manually powered movement of the frame 14'. More specifically, rotation of the movable support assembly 60 including one or more of the wheels or other moveable support member 62 causes driving rotation of each of the support shafts 36 through appropriate interconnecting linkage 48'. As schematically represented the linkage 48' is disposed in driving interconnection between the movable support assembly 60 and each of the support rods 36 associated with each of the magnetic arrays 30 and 32. It should be apparent that any of a variety of different gearing, drive belts, chain drives or mechanical linkage may define the interconnecting linkage 48'.

Figure 4:
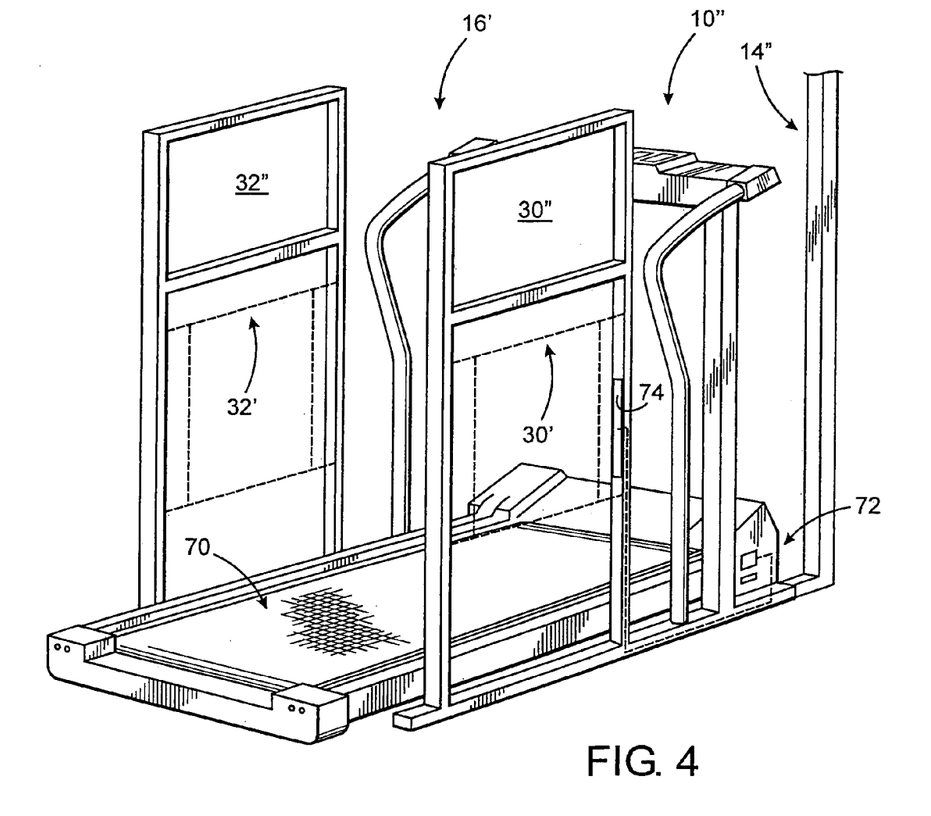
FIG. 4 is a perspective view in partial cutaway of yet another preferred embodiment of the present invention incorporating a movable support platform within a treatment area.

Yet another embodiment of the present invention is represented at least partially in schematic form in FIG. 4. More specifically the assembly 10" includes the frame 14" shown in partial cutaway and disposed in at least partially surrounding relation to the treatment area 16. Also located within the treatment area 16 is a support platform 70 which is specifically structured to facilitate walking, jogging, running, etc. of a user 12 while supported thereon. As should be apparent the preferred embodiment of FIGS. 2 and 3 define the treatment area 16 movable with the mobile frame 14'. To the contrary, in the preferred embodiment of FIG. 4, the treatment area 16 more closely resembles the treatment area 16 of the embodiment of FIG. 1 at least to the extent that the treatment area 16 and the frame 14" are intended to be stationary.

As such, a user 12 may be within the treatment area 16 in an upright position and when so disposed, the user 12 is supported on the movable support platform 70. The moveable support platform preferably, but not exclusively, comprises a treadmill assembly or other structure which electrically/mechanically operates to allow movement of the user 12 in a walking, running, jogging orientation. Also schematically represented is the inclusion of a generating assembly having at least one, but preferably a plurality of two magnetic arrays 30' and 32'. As with the embodiments of FIGS. 1 through 3, the magnetic arrays 30' and 32' are located on opposite sides of the treatment area 16 and a user 12 disposed therein. Accordingly, during walking, running, and/or jogging-type movement while supported on the movable support platform 70, the user is also being concurrently exposed to the different magnetic fields generated by the magnetic arrays 30' and 32'. The continuous movement of the one or more magnetic arrays 30', 32' may be accomplished by a power take-off assembly, generally indicated as 72, being connected to the driving mechanism of the treadmill assembly 70. The power take-off assembly 72 is also interconnected to an auxiliary drive assembly 74 which may be associated with each of the magnetic arrays 30', 32'. Further, supplementary magnetic arrays schematically represented as 30" and 30"', may also be oriented in a somewhat stacked orientation on one or both sides of the treatment area 16. This will further assure the provision of a maximum exposure of generated, moving magnetic fields to a user 12 within the treatment area 16 associated with the frame 14".

Figure 5:
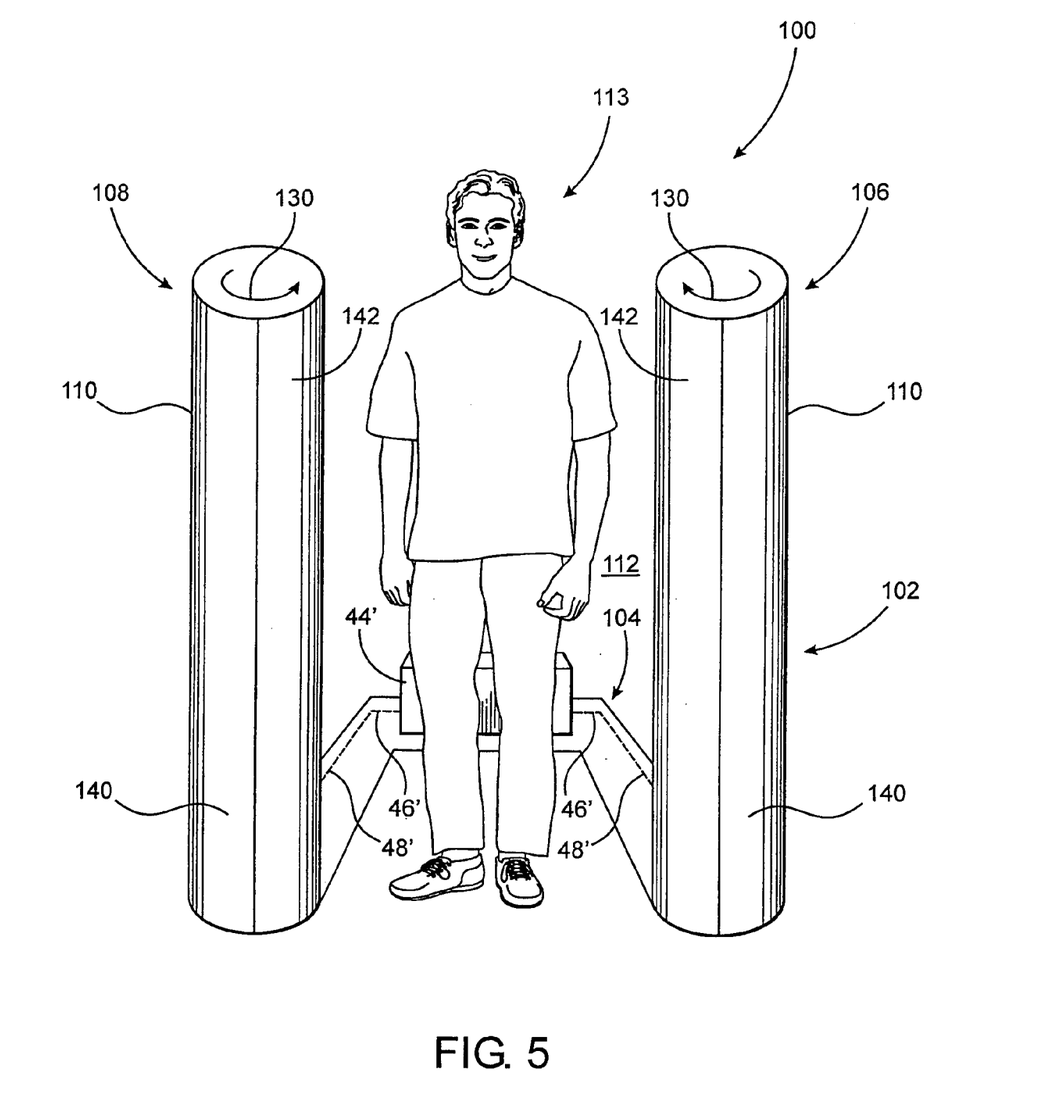
FIG. 5 is a front perspective view of yet another preferred embodiment of the assembly of the present invention.
Figure 6:
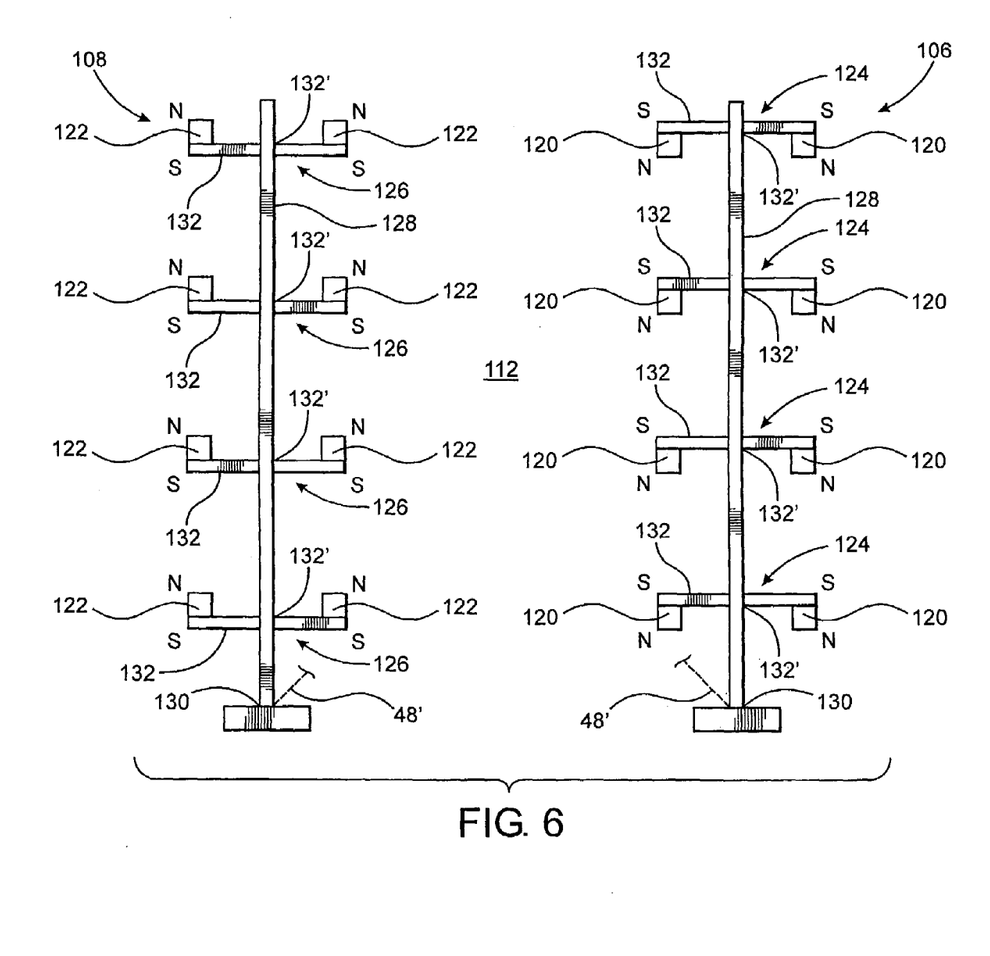
FIG. 6 is a front plan view of interior portions of cooperatively disposed magnetic arrays associated with the embodiment of FIG. 5.
Figure 7:
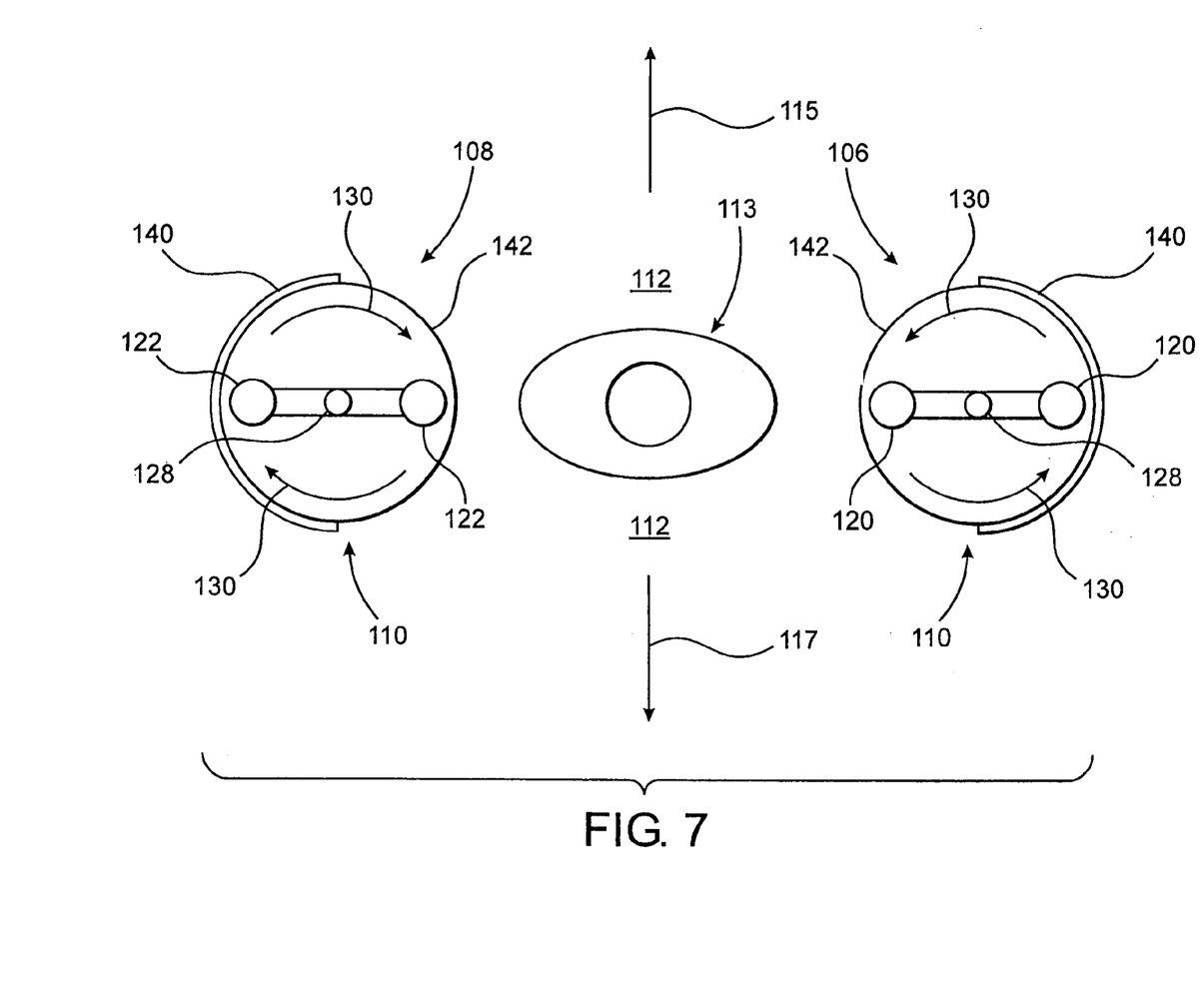
FIG. 7 is a top, at least partially interior view of the magnetic arrays of the embodiment of FIGS. 5 and 6.

With primary reference to FIGS. 5 through 7, the present invention comprises yet another most preferred embodiment represented as assembly 100. More specifically, the assembly 100, comprises a frame generally indicated as 102, including lower support or ground engaging portion generally indicated as 104 and at least one, but more practically a plurality of magnetic arrays, specifically including two magnetic arrays 106 and 108. Each of the magnetic arrays 106 and 108 include an exterior housing 110 at least partially enclosing and/or surrounding interior portions thereof as represented in FIG. 6.

For purposes of clarity, the interior portions of the magnetic arrays 106 and 108 are disclosed in FIG. 6 absent the structural features of the aforementioned housings 110. Accordingly, the assembly comprises a generating assembly at least partially defined by the plurality of magnetic arrays 106 and 108, wherein the generating assembly, through operation of the magnetic arrays 106 and 108 are structured to generate magnetic fields to pass through the treatment area 112. The treatment area 112 is generally defined between the magnetic arrays 106 and 108, wherein the treatment area 112 is preferably associated with the frame 102, which may include a support surface or ground engaging portion 104. In addition, the treatment area 112 is dimensioned, disposed and configured to accommodate a user 113 therein, wherein the user may assume an upright orientation. Obviously, the dimension and configuration of the treatment area 112 is such as to allow the user 113 to assume other orientations other than an upright orientation.

Further, the treatment area 112 may be defined as the area in which the user 113 is positionable so as to be exposed to the aforementioned magnetic fields generated by activation of the magnetic arrays 106 and 108 which define the aforementioned generating assembly. As will become apparent by the following detailed description of the operative and structural features of the assembly 100, the actual location, size, configuration, etc. of the treatment area 112 may vary and is not limited to a specifically precise area located immediately between and in aligned relation with the magnetic arrays 106 and 108. As an alternative to the representation of the treatment area 112 and the user 113 of FIG. 7, the user 113 can be located an additional distance forward, as indicated by directional arrow 115, or an additional distance rearward, as indicated by directional arrow 117. In any event and regardless of the specific structural modifications or variations of the assembly 100, a preferred treatment area 112 is that area located generally between the magnetic arrays 106 and 108 where the user 113 receives a maximum or other predetermined degree of exposure to the magnetic fields generated by both of the magnetic arrays 106 and 108.

Again with reference to FIG. 6, each of the magnetic arrays 106 and 108 comprise a plurality of magnets correspondingly indicated as 120 and 122. Moreover, the plurality of magnets 120 at least partially define a plurality of magnetic assemblies 124 and the plurality of magnets 122 at least partially define a plurality of magnetic assemblies 126. Further, each of the plurality of magnets 120 and 122 comprise a north pole and south pole as schematically indicated. It is further noted that in a most preferred embodiment of the assembly 100, the plurality of magnets 120 of the magnetic array 106 are disposed and/or mounted to have reversed orientations relative to the plurality of magnets 122, wherein such a reversed orientation is indicated by the locations of the north pole and south pole as also clearly represented in FIG. 6. The reversed orientations of the plurality of magnets 120 and 122 facilitates generation of a preferred, maximum or other predetermined strength and orientation of the magnetic fields. Further structural and operative variations of the present invention include the plurality of magnets 120 and 122 being either permanent magnets or electromagnets. When electromagnets are utilized they are connected to appropriate electrical circuitry (not shown) so as to vary the current flow thereto, thereby further regulating the respective magnetic fields generated thereby.

Also, the plurality of magnets 120 and 122 as well as the respective or corresponding magnetic assemblies 124 and 126 with which they area associated may vary in structure, dimension, configuration and disposition. However, regardless of the structuring of the plurality of magnets 120 and 122, being either permanent or electromagnets, the strength or intensity thereof must be sufficient to expose the user 113, when located within the treatment area 112, to continuously moving magnetic fields generated by each of the magnetic arrays 106 and 108. As will be more apparent from the description hereinafter provided, movable magnetic fields, relative to the treatment area 112 are generated by movement of interior portions of the magnetic arrays 106 and 108.

More specifically, interior portions, as schematically represented in FIG. 6, of each of the magnetic arrays 106 and 108 preferably comprise a base defined by an elongated stanchion or support member 128 being rotationally disposed on opposite sides of the treatment area 112. As such, each of the stanchions 128 has a lower or other appropriate portion thereof mounted in a bearing assembly or journal box 130 to facilitate continuous and efficient rotation thereof when driven by a motor or like drive assembly 44' represented in FIG. 5.

Similar to the embodiment of FIG. 1, the drive assembly 44' may be in the form of an electrically or otherwise powered drive motor having one or more power take-off structures are preferably disposed within the interior of the support surface or ground engaging portion 104 as indicated in phantom lines as 46'. In addition, interconnecting linkage, schematically indicated as 48', serve to drivingly interconnect the power take-off structures 46' to bearing assemblies or journal boxes 130 of each stanchion 128 associated with the magnetic arrays 106 and 108. Activation of the drive assembly 44' will cause a concurrent rotation of each of the stanchions 128 in opposite directions, wherein such rotation will preferably be synchronized due to the structuring or the interconnection of the associated linkage 48' as represented in FIG. 5. Moreover, the rotation of the stanchions 128 and accordingly the plurality magnetic assemblies 124 and 126 associated therewith in opposition directions is schematically represented by the rotational directional arrows 130 of FIG. 5 and FIG. 7. Therefore, continuous operation of the drive assembly 44' will cause continuous rotation of each of the stanchions 128, at least partially defining corresponding ones of the magnetic arrays 106 and 108.

Again with primary reference to FIGS. 6 and 7, additional structural details of at least one preferred embodiment of the plurality of magnetic assemblies 124 and 126 comprise each of the magnetic assemblies 124 and 126 including at least two spaced apart magnets 120 and 122, as indicated. Further, lateral spacing of the magnets 120 and 122 is accomplished by their connection, support and/or mounting on one or more support structures or arms 132. As such, the plurality of magnets 120 and 122 are located, in the aforementioned reversed orientation on the outermost ends of the support members or arms 132 in a lateral spaced relation to one another. As such, each of the plurality of magnets 120 and 122 extend radially outward from a corresponding stanchion 128 by means of the support arms or structures 132 being fixedly or otherwise attached to the respective stanchions 128 such as, but not limited to at a midpoint of the support arms 132 as at 132'.

Accordingly, a preferred fixed connection or attachment of the support arms 132 to the respective stanchions 128 will facilitate rotation of each of the plurality of magnetic assemblies 124 and 126 upon the rotation of the respective stanchions 128. As indicated above, the structure and disposition of the connecting linkage 48' will be such as to cause the stanchions 128 to rotate in opposite directions, as indicated by directional arrows 130. Accordingly, each of the magnetic assemblies 124 will rotate in an opposite direction to the plurality of magnetic assemblies 126 associated with the different magnetic arrays 106 and 108.

As emphasized above, maximum therapeutic benefits to a user 113 utilizing the various embodiments of the assembly as at 10 and 100 of the present invention is based, at least in part, on maximum or at least adequate exposure to the moving magnetic fields which move or pass through the treatment area of the respective embodiments. Therefore, with reference to the preferred embodiments of FIGS. 5 though 7 each of the magnetic arrays 106 and 108 include an aforementioned, exteriorly located housing 110 which at least partially surrounds or encloses the plurality of magnetic assemblies 124 and 126 as well as the base or stanchion members 128 and the plurality of corresponding magnets 120 and 122 associated therewith. Moreover, each of the housings 110 include a barrier portion as at 140 extending preferably along an outer or exterior side portion of the respective housing 110 as demonstrated in FIG. 7. These barrier structures 140 are formed from any one of a plurality of materials which are resistant to the passage of magnetic flux or the magnetic field therethrough. Such materials may include aluminum or other materials of relatively low conductivity.

In contrast, the housing 110 further includes the inner half or like portion 142 which may be structured for the passage there through of the magnetic fields generated by the respective magnetic arrays 106 and 108. As such, the material from which the inner portions 142 of the housings 110 are formed may be a plastic such as, but not limited to, acetate, which does not interfere with the passage of the respective magnetic fields generated by the magnetic arrays 106 and 108 therethrough. With reference to FIG. 5, in one preferred structural modification or embodiment of the assembly 10, both the barrier portions 140 and the opposite, inner wall portions 142 of the respective housings 110 may extend along substantially the entire length of the housings 110 in order to restrict, limit or at least partially control the direction, travel or flow of the magnetic fields generated by the respective magnetic arrays 106 and 108. More specifically, the positioning of the barrier structures 140 on the outer side or portion of the housings 110 serves to prohibit or limit the passage of the generated magnetic fields to the outer side, front and rear portions of the housings 110 dependent upon the specific disposition, configuration and dimension of the barrier structures 140.

In contrast the magnetic fields generated by each of the magnetic arrays 106 and 108 are channeled or at least somewhat restricted to flow into and through the treatment area 112 so as to provide meaningful or maximum exposure of the user 113 thereto.

Further with regard to FIG. 6, one preferred embodiment of the assembly 10 comprises each of the magnetic arrays 106 and 108 having an elongated, substantially vertical orientation substantially in accord with the dimension, configuration and disposition of the respective housings 110 and stanchions 128. As should be noted, the height or length or the magnetic arrays 106 and 108 may vary but is preferably sufficient to extend above and or in at least general alignment with the height of a generally sized user 113. Also, the generation of a predetermined, meaningful and possibly maximum magnetic field by each of the magnetic arrays 106 and 108 may be accomplished, in at least one embodiment, by the vertical spacing of each of the magnetic assemblies 124 relative to one another along at least a portion of the length of the corresponding base stanchion 128. Similarly, each of the magnetic assemblies 126 is also vertically spaced from one another along the length of the respective base stanchion 128. It should be further noted that the member and specific spacing between the magnetic assemblies 124 and the magnetic assemblies 126 may vary. However, in at least one preferred embodiment of the assembly 100, each of the magnetic assemblies 124 is substantially aligned, in terms of height or vertical orientation with at least one of the magnetic assemblies 126 as also shown in FIG. 6.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An assembly structured to expose a user to a therapeutically beneficial magnetic field, said assembly comprising:
   a frame structured to at least partially define a treatment area,
   said treatment area dimensioned and configured to accommodate a user therein,
   a generating assembly comprising at least two magnetic arrays each disposed and structured to generate a different moving magnetic field in communication with said treatment area and a user therein,
   said magnetic arrays movable in different directions relative to said treatment area, and
   said magnetic arrays cooperatively disposed relative to said treatment area and structured to direct movement of said different magnetic fields through at least a portion of said treatment area in a common direction.

2. An assembly as recited in claim 1 wherein each of said magnetic arrays comprises a plurality of magnetic assemblies collectively and concurrently movable relative to said treatment area.

3. An assembly as recited in claim 2 wherein said plurality of magnetic assemblies of each of said magnetic arrays are collectively disposed in an elongated, stacked configuration.

4. An assembly as recited in claim 3 wherein said stacked configuration of each of said magnetic arrays is at least partially defined by corresponding ones of said magnetic assemblies disposed in vertically spaced relation to one another.

5. An assembly as recited in claim 4 wherein said plurality of magnetic assemblies of each of said magnetic arrays are collectively and concurrently rotatable relative to said treatment area.

6. An assembly as recited in claim 2 wherein said plurality of magnetic assemblies of each of said magnetic arrays are collectively and concurrently rotatable relative to said treatment area.

7. An assembly as recited in claim 6 wherein each of said magnetic assemblies comprises a plurality of magnets disposed in spaced relation to one another and collectively movable relative to said treatment area.

8. An assembly as recited in claim 7 wherein said plurality of magnets of each magnetic assembly are connected to a base and rotatable therewith relative to said treatment area.

9. An assembly as recited in claim 8 wherein said base of each of said magnetic arrays comprises a stanchion disposed in a substantially vertical orientation.

10. An assembly as recited in claim 2 wherein each of said magnetic arrays includes a base, said base comprising a stanchion disposed in a substantially vertical orientation, said stanchion having a height at least partially corresponding to the user in an upright position.

11. An assembly as recited in claim 10 wherein said plurality of magnetic assemblies of each magnetic array are collectively disposed in spaced relation to one another along at least a majority of the height of a corresponding one of said bases.

12. An assembly as recited in claim 11 wherein said plurality of magnetic assemblies are connected to and rotatable with a corresponding one of said bases relative to said treatment area.

13. An assembly as recited in claim 11 wherein said at least two magnetic arrays are located on opposite sides of said treatment area and the user contained therein.

14. An assembly as recited in claim 1 wherein said at least two magnetic arrays are located on opposite sides of said treatment area and the user contained therein.

15. An assembly as recited in claim 14 wherein each of said at least two magnetic arrays are rotatable in opposite directions relative to said treatment area.

16. An assembly as recited in claim 15 wherein each of said two magnetic arrays comprise an upright, substantially vertical orientation having a height at least partially corresponding to the user in an upright position.

17. An assembly as recited in claim 14 wherein each of said at least two magnetic arrays further comprise a housing disposed in enclosing relation to at least a portion of an interior thereof, each of said housings including a barrier structure disposed and configured to substantially limit exposure of said magnetic fields to a vicinity of said treatment area.

18. An assembly as recited in claim 17 wherein said barrier structure is formed of a material of reduced magnetic field permeability and is disposed to restrict passage of said magnetic fields beyond said vicinity of said treatment area.

19. An assembly as recited in claim 18 wherein a remaining portion of said housing, other than said barrier structure is formed of an acetate material, said other portion disposed in communicating relation to said treatment area.

20. An assembly as recited in claim 18 wherein a remaining portion of said housing, other than said barrier structure is formed of an acetate material, said other portion disposed in communicating relation to said treatment area.

21. An assembly structured to expose a user to a therapeutically beneficial magnetic field, said assembly comprising:
a frame disposed adjacent to and at least partially defining a treatment area,
said treatment area dimensioned and configured to accommodate a user therein,
a generating assembly comprising at least two magnetic arrays each disposed on an opposite side of said treatment area and each structured to generate a different magnetic field in communication with said treatment area and a user therein,
each of said magnetic arrays comprising an elongate, substantially vertical configuration of sufficient height to accommodate exposure of the user when at least partially in an upright orientation, said magnetic arrays being concurrently movable relative to said treatment area, and each of said magnetic arrays disposed and structured to generate a magnetic field movable through said treatment area in a common direction.

22. An assembly as recited in claim 21 wherein each of said magnetic arrays comprises a plurality of magnetic assemblies collectively and concurrently movable relative to said treatment area.

23. An assembly as recited in claim 22 wherein each of said magnetic arrays is at least partially defined by said magnetic assemblies disposed in a stacked configuration, said stacked configuration at least partially defined by a substantially vertically spaced relation to one another.

24. An assembly as recited in claim 23 wherein said plurality of magnetic assemblies of each of said magnetic arrays are collectively and concurrently rotatable relative to said treatment area.

25. An assembly as recited in claim 24 wherein each of said plurality of magnetic assemblies comprises a plurality of magnets disposed in laterally spaced relation to one another and collectively movable relative to said treatment area.

26. An assembly as recited in claim 21 wherein each of said two magnetic arrays further comprise a housing disposed in enclosing relation to at least a portion of an interior thereof, each of said housings include a barrier structure disposed and configured to substantially direct exposure of magnetic fields to a vicinity of said treatment area.

27. An assembly as recited in claim 24 wherein said barrier is formed of a material of reduced magnetic permeability and is disposed to restrict passage of said magnetic field beyond said treatment area.

* * * * *